United States Patent
Saygili et al.

(10) Patent No.: US 11,406,773 B2
(45) Date of Patent: Aug. 9, 2022

(54) CARTRIDGE ASSEMBLY WITH VENTILATION AIRFLOW

(71) Applicant: Philip Morris Products S.A., Neuchatel (CH)

(72) Inventors: Ali Murat Saygili, Neuchatel (CH); Patrick Charles Silvestrini, Neuchatel (CH)

(73) Assignee: Philip Morris Products S.A., Neuchatel (CH)

(*) Notice: Subject to any disclaimer, the term of this patent is extended or adjusted under 35 U.S.C. 154(b) by 372 days.

(21) Appl. No.: 16/621,326

(22) PCT Filed: Jul. 10, 2018

(86) PCT No.: PCT/EP2018/068708
§ 371 (c)(1),
(2) Date: Dec. 11, 2019

(87) PCT Pub. No.: WO2019/011937
PCT Pub. Date: Jan. 17, 2019

(65) Prior Publication Data
US 2020/0163376 A1 May 28, 2020

(30) Foreign Application Priority Data

Jul. 10, 2017 (EP) .................................... 17180610

(51) Int. Cl.
*A24B 15/167* (2020.01)
*A24F 40/42* (2020.01)
*A24F 40/30* (2020.01)
(Continued)

(52) U.S. Cl.
CPC ......... *A61M 11/042* (2014.02); *A24B 15/167* (2016.11); *A24F 40/42* (2020.01);
(Continued)

(58) Field of Classification Search
CPC .......... A24F 40/40; A24F 40/42; A24F 40/20; A61M 15/06
See application file for complete search history.

(56) References Cited

U.S. PATENT DOCUMENTS 9,451,793 B2 * 9/2016 Zhou ...................... A61M 15/06
2016/0022930 A1 * 1/2016 Greim ................... A61M 15/06
131/328
(Continued)

FOREIGN PATENT DOCUMENTS

EP 2 991 516 B1 11/2016
RU 157 882 U1 12/2015
(Continued)

OTHER PUBLICATIONS

Combined Russian Office Action and Search Report dated Sep. 30, 2021 in Russian Patent Application No. 2019141812 (with English Translation), 15 pages.
(Continued)

*Primary Examiner* — Anthony Calandra
(74) *Attorney, Agent, or Firm* — Oblon, McClelland, Maier & Neustadt, L.L.P.

(57) ABSTRACT

A cartridge assembly for an aerosol-generating system is provided, including a cartridge having upstream and downstream ends, a first compartment having a first air inlet and a first air outlet, and a second compartment having a second air inlet and a second air outlet; a cartridge holder, a portion of the cartridge being received within the cartridge holder; a mouthpiece having upstream and downstream ends, at least a portion of the cartridge holder is received within the mouthpiece, the downstream end of the cartridge is spaced apart from the downstream end of the mouthpiece and defines a mixing chamber therebetween, and another portion of the cartridge holder is spaced apart from the mouthpiece and defines an airflow channel between the cartridge holder
(Continued)

and the mouthpiece; and a ventilation air aperture providing fluid communication between a downstream portion of the airflow channel and the mixing chamber.

15 Claims, 2 Drawing Sheets

(51) Int. Cl.
    *A24F 40/20*     (2020.01)
    *A61M 11/04*     (2006.01)
    *A24F 40/57*     (2020.01)
    *A24F 40/485*     (2020.01)

(52) U.S. Cl.
    CPC ............ *A24F 40/485* (2020.01); *A24F 40/57* (2020.01); *A24F 40/20* (2020.01); *A24F 40/30* (2020.01); *A61M 2205/123* (2013.01); *A61M 2205/8206* (2013.01)

(56) References Cited

U.S. PATENT DOCUMENTS

| | | | |
|---|---|---|---|
| 2016/0089508 A1* | 3/2016 | Smith | A61M 15/0085 128/202.21 |
| 2016/0120221 A1 | 5/2016 | Mironov et al. | |
| 2017/0049155 A1* | 2/2017 | Liu | H05B 1/0244 |
| 2017/0095002 A1 | 4/2017 | Silvestrini | |
| 2017/0258140 A1* | 9/2017 | Rostami | A24F 40/48 |
| 2017/0347715 A1 | 12/2017 | Mironov et al. | |
| 2018/0228216 A1* | 8/2018 | Saygili | A61M 11/042 |
| 2019/0124982 A1* | 5/2019 | Atkins | A24F 40/30 |
| 2019/0350262 A1* | 11/2019 | Saygili | H05B 6/108 |
| 2021/0145051 A1* | 5/2021 | Florack | A24F 40/48 |

FOREIGN PATENT DOCUMENTS

| | | |
|---|---|---|
| WO | WO 2015/177046 A1 | 11/2015 |
| WO | WO 2015/197627 A1 | 12/2015 |
| WO | WO 2017/032695 A1 | 3/2017 |
| WO | WO 2017/108721 A1 | 6/2017 |
| WO | WO 2018/099999 A1 | 6/2018 |

OTHER PUBLICATIONS

International Search Report and Written Opinion dated Aug. 2, 2018 in PCT/EP2018/068708 filed on Jul. 10, 2018.

* cited by examiner

CARTRIDGE ASSEMBLY WITH VENTILATION AIRFLOW

The present invention relates to a cartridge assembly for an aerosol-generating system, the cartridge assembly configured for ventilation airflow through the cartridge assembly. The present invention also relates to an aerosol-generating system comprising the cartridge assembly. Particularly preferred embodiments of the invention relate to a cartridge assembly comprising a nicotine source and acid source for use in an aerosol-generating system for the in situ generation of an aerosol comprising nicotine salt particles and an aerosol-generating system comprising such a cartridge assembly.

Devices for generating and delivering aerosols to a user are known, including devices for delivering nicotine to a user. Known systems for delivering aerosols to a user may include one or more inlets for introducing ventilation air into the device. In this context, ventilation air is airflow that passes through the system in a manner that bypasses the aerosol-generating section of the system. Therefore, ventilation air dilutes the mainstream airflow containing the generated aerosol to provide a desired concentration of aerosol to the user.

However, typically, known devices have included ventilation air inlets without considering the effect of ventilation air on the quality of the aerosol delivered to a user and how positioning ventilation air inlets may affect usability of the device. It would be desirable to provide an aerosol-generating system that addresses at least these issues with known devices.

According to a first aspect of the present invention there is provided a cartridge assembly for an aerosol-generating system, the cartridge assembly comprising a cartridge having an upstream end and a downstream end. The cartridge comprises a first compartment having a first air inlet at the upstream end of the cartridge and a first air outlet at the downstream end of the cartridge, and a second compartment having a second air inlet at the upstream end of the cartridge and a second air outlet at the downstream end of the cartridge. The cartridge assembly further comprises a cartridge holder, wherein at least a portion of the cartridge is received within the cartridge holder. The cartridge assembly also comprises a mouthpiece having an upstream end and a downstream end, wherein at least a portion of the cartridge holder is received within the mouthpiece. The downstream end of the cartridge is spaced apart from the downstream end of the mouthpiece to define a mixing chamber between the downstream end of the cartridge and the downstream end of the mouthpiece. A portion of the cartridge holder is spaced apart from the mouthpiece to define an airflow channel between the cartridge holder and the mouthpiece. The cartridge assembly also comprises a ventilation air aperture providing fluid communication between a downstream portion of the airflow channel and the mixing chamber.

As used herein, the terms "upstream" and "downstream" refer to the direction of airflow through the cartridge assembly or components of the cartridge assembly during use of the cartridge assembly in an aerosol-generating system. That is, generally, air flows from an upstream end to a downstream end.

Cartridge assemblies according to the present invention comprise an airflow channel positioned between a cartridge holder and a mouthpiece, and a ventilation aperture providing fluid communication between a downstream portion of the airflow channel and a mixing chamber downstream of a cartridge. The present inventors have recognised that this configuration is particularly advantageous when compared to known aerosol-generating systems.

Firstly, ventilation air flowing through the airflow channel during use of the cartridge assembly is insulated by the cartridge holder from the cartridge, which is typically heated during use. Advantageously, this reduces the temperature of the ventilation air when compared to known systems in which ventilation air enters the system upstream of the cartridge or at an upstream end of the cartridge and flows across an outer surface of the cartridge before being mixed with mainstream air further downstream. Reducing the temperature of the ventilation air may reduce the overall temperature of the aerosol delivered to a user, which may improve the user experience. Reducing the temperature of the ventilation air may facilitate an increase in a heating temperature of the cartridge while maintaining an overall temperature of the aerosol delivered to a user.

Secondly, providing an airflow channel between the cartridge holder and the mouthpiece with a ventilation aperture at a downstream portion of the airflow channel may facilitate an improved placement of a ventilation air inlet on an outer surface of an aerosol-generating system comprising the cartridge assembly. For example, although the ventilation aperture delivers ventilation air to a mixing chamber towards a downstream end of the cartridge assembly, an aerosol-generating system comprising the cartridge assembly may comprise a ventilation air inlet proximate an upstream end of the cartridge assembly and in fluid communication with an upstream end of the airflow channel. Advantageously, this may reduce the risk of a user's mouth obscuring the ventilation air inlet when compared to known systems in which a ventilation air inlet is provided proximate a downstream end of a mouthpiece to deliver ventilation air directly into a mixing chamber.

The ventilation air aperture may be provided on the cartridge holder in a region of overlap between the cartridge holder and the cartridge. The cartridge has a total length extending between its upstream end and its downstream end. To maintain a reduced temperature of the ventilation air entering the mixing chamber, the distance in the downstream direction between the ventilation air aperture and the downstream end of the cartridge is less than about 50 percent of the total length of the cartridge. The distance in the downstream direction between the ventilation air aperture and the downstream end of the cartridge is preferably less than about 40 percent of the total length of the cartridge. The distance in the downstream direction between the ventilation air aperture and the downstream end of the cartridge is more preferably less than about 30 percent of the total length of the cartridge. The distance in the downstream direction between the ventilation air aperture and the downstream end of the cartridge is more preferably less than about 20 percent of the total length of the cartridge. The distance in the downstream direction between the ventilation air aperture and the downstream end of the cartridge is more preferably less than about 10 percent of the total length of the cartridge. Advantageously, reducing the distance between the ventilation air aperture and the downstream end of the cartridge reduces the temperature of the ventilation air entering the mixing chamber by reducing contact between the cartridge and the ventilation air. Preferably, a portion of the cartridge is spaced apart from a portion of the cartridge holder between the ventilation air aperture and the mixing chamber to provide fluid communication between the ventilation air aperture and the mixing chamber.

Preferably, the ventilation air aperture is positioned downstream of the downstream end of the cartridge. Advantageously, this configuration may minimise the temperature of the ventilation air entering the mixing chamber by eliminating contact between the ventilation air and the cartridge prior to the ventilation air entering the mixing chamber. Preferably, the ventilation air aperture is positioned at a downstream end of the airflow channel.

The cartridge may define a longitudinal direction extending between its upstream end and its downstream end and a radial direction orthogonal to the longitudinal direction. Preferably, at least a portion of the airflow channel is positioned radially outward from the cartridge.

Advantageously, positioning at least a portion of the airflow channel radially outward from the cartridge may facilitate shortening of the cartridge assembly by allowing ventilation air to flow through the cartridge assembly in parallel with airflow through the first and second compartments of the cartridge.

Advantageously, positioning at least a portion of the airflow channel radially outward from the cartridge may facilitate positioning of a ventilation air inlet in a system comprising the cartridge assembly towards an upstream end of the cartridge assembly.

The mouthpiece may comprise a tubular part in which the at least a portion of the cartridge holder is received, a downstream part extending across a downstream end of the tubular part, and a mouthpiece air outlet in the downstream part. The mouthpiece air outlet provides fluid communication between the mixing chamber and the exterior of the cartridge assembly.

Advantageously, the tubular part may be shaped to optimise insertion of the cartridge holder into the mouthpiece during manufacture of the cartridge assembly.

Advantageously, the mouthpiece part may be shaped to facilitate an ergonomic interaction with a user's mouth. The mouthpiece part may have a cross-sectional area that decreases in a downstream direction. That is, the mouthpiece part may have a tapered cross-sectional shape.

The tubular part and the downstream part may be formed separately and joined together during manufacture. Preferably, the tubular part and the downstream part are integrally formed. For example, the tubular part and the downstream part may be formed as a single piece during a moulding process.

At least a portion of a downstream end of the cartridge holder may be spaced apart from the downstream part of the mouthpiece to form a first gap between the downstream end of the cartridge holder and the downstream part of the mouthpiece, the first gap forming the ventilation air aperture. Advantageously, this arrangement may eliminate the need to form a discrete ventilation air aperture in one or more components of the cartridge assembly. That is, the ventilation air aperture may be formed between the cartridge holder and the mouthpiece upon insertion of the cartridge holder into the mouthpiece during manufacture of the cartridge assembly.

The cartridge holder may define the ventilation air aperture. That is, the ventilation air aperture may extend through a portion of the cartridge holder. Advantageously, this arrangement may facilitate precise control over the size of the ventilation air aperture, which may provide a desired flow of ventilation air into the mixing chamber during use of the cartridge assembly.

The cartridge assembly may comprise a single ventilation air aperture. The cartridge assembly may comprise a plurality of ventilation air apertures. The skilled person can select the number of ventilation air apertures to provide a desired flow of ventilation air into the mixing chamber during use of the cartridge assembly.

Preferably, the cartridge holder comprises a tubular part in which the at least a portion of the cartridge is received. Preferably, the tubular part comprises an open upstream end through which the cartridge is inserted into the tubular part during manufacture of the cartridge assembly. Preferably, the tubular part comprises an open downstream end to provide fluid communication between the first and second air outlets of the cartridge and the mixing chamber.

In embodiments in which the cartridge assembly defines the ventilation air aperture, preferably the ventilation air aperture extends through a downstream portion of the tubular part of the cartridge holder.

Preferably, at least a portion of the upstream end of mouthpiece is spaced apart from an upstream end of the cartridge holder to define a third air inlet, the third air inlet forming an upstream end of the airflow channel. The cartridge assembly may be configured so that, in an aerosol-generating system comprising the cartridge assembly, the third air inlet forms a ventilation air inlet providing fluid communication between an exterior of the aerosol-generating system and the airflow channel. The cartridge assembly may be configured so that the third air inlet is in fluid communication with a ventilation air inlet of an aerosol-generating system comprising the cartridge assembly.

Preferably, the first compartment contains a first aerosol-forming substrate and the second compartment contains a second aerosol-forming substrate.

Preferably, the first compartment contains a nicotine source and the second compartment contains an acid source. As described herein, the configuration of cartridge assemblies according to the present invention may facilitate a reduction in the temperature of ventilation air entering the mixing chamber. The present inventors have recognised that this is particularly advantageous in embodiments in which the cartridge comprises a nicotine source and an acid source, wherein nicotine and acid vapours are mixed in the mixing chamber to form nicotine salt particles for delivery to a user. In particular, the present inventors have recognised that reducing the temperature of the ventilation air entering the mixing chamber reduces the mean size of the nicotine salt particles formed within the mixing chamber, which advantageously reduces the harshness of the aerosol perceived by a user. Specifically, mixing ventilation air entering the mixing chamber at a temperature of below 50 degrees Celsius with nicotine and acid vapours both entering the mixing chamber at a temperature of approximately 80 degrees Celsius results in a significant reduction in nicotine salt particles having a diameter of over 2 micrometres, which yields the reduction in perceived harshness.

The nicotine source may comprise a first carrier material impregnated with between about 1 milligram and about 50 milligrams of nicotine. The nicotine source may comprise a first carrier material impregnated with between about 1 milligram and about 40 milligrams of nicotine. Preferably, the nicotine source comprises a first carrier material impregnated with between about 3 milligrams and about 30 milligrams of nicotine. More preferably, the nicotine source comprises a first carrier material impregnated with between about 6 milligrams and about 20 milligrams of nicotine. Most preferably, the nicotine source comprises a first carrier material impregnated with between about 8 milligrams and about 18 milligrams of nicotine.

The first carrier material may be impregnated with liquid nicotine or a solution of nicotine in an aqueous or non-aqueous solvent.

The first carrier material may be impregnated with natural nicotine or synthetic nicotine.

The acid source may comprise an organic acid or an inorganic acid.

Preferably, the acid source comprises an organic acid, more preferably a carboxylic acid, most preferably an alpha-keto or 2-oxo acid or lactic acid.

Advantageously, the acid source comprises an acid selected from the group consisting of 3-methyl-2-oxopentanoic acid, pyruvic acid, 2-oxopentanoic acid, 4-methyl-2-oxopentanoic acid, 3-methyl-2-oxobutanoic acid, 2-oxooctanoic acid, lactic acid and combinations thereof. Advantageously, the acid source comprises pyruvic acid or lactic acid. More advantageously, the acid source comprises lactic acid.

Advantageously, the acid source comprises a second carrier material impregnated with acid.

The first carrier material and the second carrier material may be the same or different.

Advantageously, the first carrier material and the second carrier material have a density of between about 0.1 grams/cubic centimetre and about 0.3 grams/cubic centimetre.

Advantageously, the first carrier material and the second carrier material have a porosity of between about 15 percent and about 55 percent.

The first carrier material and the second carrier material may comprise one or more of glass, cellulose, ceramic, stainless steel, aluminium, polyethylene (PE), polypropylene, polyethylene terephthalate (PET), poly(cyclohexanedimethylene terephthalate) (PCT), polybutylene terephthalate (PBT), polytetrafluoroethylene (PTFE), expanded polytetrafluoroethylene (ePTFE), and BAREX®.

The first carrier material acts as a reservoir for the nicotine.

Advantageously, the first carrier material is chemically inert with respect to nicotine.

The first carrier material may have any suitable shape and size. For example, the first carrier material may be in the form of a sheet or plug.

Advantageously, the shape and size of the first carrier material is similar to the shape and size of the first compartment of the cartridge.

The shape, size, density and porosity of the first carrier material may be chosen to allow the first carrier material to be impregnated with a desired amount of nicotine.

Advantageously, the first compartment of the cartridge may further comprise a flavourant. Suitable flavourants include, but are not limited to, menthol.

Advantageously, the first carrier material may be impregnated with between about 3 milligrams and about 12 milligrams of flavourant.

The second carrier material acts as a reservoir for the acid.

Advantageously, the second carrier material is chemically inert with respect to the acid.

The second carrier material may have any suitable shape and size. For example, the second carrier material may be in the form of a sheet or plug.

Advantageously, the shape and size of the second carrier material is similar to the shape and size of the second compartment of the cartridge.

The shape, size, density and porosity of the second carrier material may be chosen to allow the second carrier material to be impregnated with a desired amount of acid.

Advantageously, acid source is a lactic acid source comprising a second carrier material impregnated with between about 2 milligrams and about 60 milligrams of lactic acid.

Preferably, the lactic acid source comprises a second carrier material impregnated with between about 5 milligrams and about 50 milligrams of lactic acid. More preferably, the lactic acid source comprises a second carrier material impregnated with between about 8 milligrams and about 40 milligrams of lactic acid. Most preferably, the lactic acid source comprises a second carrier material impregnated with between about 10 milligrams and about 30 milligrams of lactic acid.

The shape and dimensions of the first compartment of the cartridge may be chosen to allow a desired amount of nicotine to be housed in the cartridge.

The shape and dimensions of the second compartment of the cartridge may be chosen to allow a desired amount of acid to be housed in the cartridge.

The ratio of nicotine and acid required to achieve an appropriate reaction stoichiometry may be controlled and balanced through variation of the volume of the first compartment relative to the volume of the second compartment.

The first air inlet of the first compartment of the cartridge and the second air inlet of the second compartment of the cartridge may each comprise one or more apertures. For example, the first air inlet of the first compartment of the cartridge and the second air inlet of the second compartment of the cartridge may each comprise one, two, three, four, five, six or seven apertures.

The first air inlet of the first compartment of the cartridge and the second air inlet of the second compartment of the cartridge may comprise the same or different numbers of apertures.

Advantageously, the first air inlet and the second air inlet each comprise a plurality of apertures. For example, the first air inlet and the second air inlet may each comprise two, three, four, five, six or seven apertures.

Providing a first air inlet comprising a plurality of apertures and a second air inlet comprising a plurality of apertures may advantageously result in more homogeneous airflow within the first compartment and the second compartment, respectively. In use, this may improve entrainment of nicotine in an air stream drawn through the first compartment and improve entrainment of acid in an air stream drawn through the second compartment.

The ratio of nicotine and acid required to achieve an appropriate reaction stoichiometry may be controlled and balanced through variation of the volumetric airflow through the first compartment relative to the volumetric airflow through the second compartment. The ratio of the volumetric airflow through the first compartment relative to the volumetric airflow through the second compartment may be controlled through variation of one or more of the number, dimensions and location of the apertures forming the first air inlet of the first compartment relative to the number, dimensions and location of the apertures forming the second air inlet of the second compartment.

In embodiments in which the acid source comprises lactic acid, advantageously the flow area of the second air inlet of the second compartment is greater than the flow area of the first air inlet of the first compartment.

As used herein with reference to the invention, the term "flow area" is used to describe the cross-sectional area of an air inlet or air outlet through which air flows during use. In embodiments in which an air inlet or air outlet comprises a plurality of apertures, the flow area of the air inlet or air outlet is the total flow area of the air inlet or air outlet and is equal to the sum of the flow areas of each of the plurality of apertures forming the air inlet or air outlet. In embodiments in which the cross-sectional area of an air inlet or air outlet varies in the direction of airflow, the flow area of the air inlet or air outlet is the minimum cross-sectional area in the direction of airflow.

The first air outlet of the first compartment of the cartridge and the second air outlet of the second compartment of the cartridge may each comprise one or more apertures. For example, the first air outlet and the second air outlet may each comprise one, two, three, four, five, six or seven apertures.

The first air outlet and the second air outlet may comprise the same or different numbers of apertures.

Advantageously, the first air outlet and the second air outlet may each comprise a plurality of apertures. For example, the first air outlet and the second air outlet may each comprise two, three, four, five, six or seven apertures. Providing a first air outlet comprising a plurality of apertures and a second air outlet comprising a plurality of apertures may advantageously result in more homogeneous airflow within the first compartment and the second compartment, respectively. In use, this may improve entrainment of nicotine in an air stream drawn through the first compartment and improve entrainment of acid in an air stream drawn through the second compartment.

In embodiments in which the first air outlet comprises a plurality of apertures, advantageously the first air outlet comprises between 2 and 5 apertures.

In embodiments in which the second air outlet comprises a plurality of apertures, advantageously, the second air outlet comprises between 3 and 7 apertures.

Advantageously, the first air outlet and the second air outlet may each comprise a single aperture, which may advantageously simplify manufacturing of the cartridge.

The ratio of nicotine and acid required to achieve an appropriate reaction stoichiometry may be controlled and balanced through variation of the volumetric airflow through the first compartment relative to the volumetric airflow through the second compartment. The ratio of the volumetric airflow through the first compartment relative to the volumetric airflow through the second compartment may be controlled through variation of one or more of the number, dimensions and location of the apertures forming the first air outlet relative to the number, dimensions and location of the apertures forming the second air outlet.

The flow area of the first air outlet may be the same as or different to the flow area of the second air outlet.

The flow area of the second air outlet may be greater than flow area of the first air outlet.

Increasing the flow area of the second air outlet relative to the flow area of the first air outlet may advantageously increase the volumetric airflow through the second air outlet compared to the volumetric airflow through the first air outlet.

The cartridge assembly may comprise one or more aerosol-modifying agents positioned within the mouthpiece. For example, the mouthpiece may contain one or more sorbents, one or more flavourants, one or more chemesthetic agents or a combination thereof.

The cartridge, the cartridge holder and the mouthpiece may be formed from any suitable material or combination of materials. Suitable materials include, but are not limited to, aluminium, polyether ether ketone (PEEK), polyimides, such as Kapton®, polyethylene terephthalate (PET), polyethylene (PE), high-density polyethylene (HDPE), polypropylene (PP), polystyrene (PS), fluorinated ethylene propylene (FEP), polytetrafluoroethylene (PTFE), polyoxymethylene (POM), epoxy resins, polyurethane resins, vinyl resins, liquid crystal polymers (LCP) and modified LCPs, such as LCPs with graphite or glass fibres.

The cartridge, the cartridge holder and the mouthpiece may be formed from the same or different materials.

The cartridge may be formed from one or more materials that are nicotine-resistant and acid-resistant.

The first compartment may be coated with one or more nicotine-resistant materials and the second compartment may be coated with one or more acid-resistant materials.

Examples of suitable nicotine-resistant materials and acid-resistant materials include, but are not limited to, polyethylene (PE), polypropylene (PP), polystyrene (PS), fluorinated ethylene propylene (FEP), polytetrafluoroethylene (PTFE), epoxy resins, polyurethane resins, vinyl resins and combinations thereof.

Use of one or more nicotine-resistant materials may advantageously enhance the shelf life of the cartridge assembly.

Use of one or more acid-resistant materials may advantageously enhance the shelf life of the cartridge assembly.

The cartridge may further comprise a third compartment positioned between the first compartment and the second compartment. Preferably, the third compartment is configured for heating the first and second compartments during use of the cartridge assembly in an aerosol-generating system. For example, the third compartment may be configured to receive a heater of an aerosol-generating device.

Preferably, the third compartment has an open upstream end and a closed downstream end.

The cartridge may further comprise a susceptor material positioned within the third compartment. Advantageously, the susceptor material may facilitate heating of the first and second compartments when the cartridge assembly is combined with an aerosol-generating device comprising an inductive heater.

According to a second aspect of the present invention there is provided an aerosol-generating system comprising an aerosol-generating device and a cartridge assembly according to the first aspect of the present invention, in accordance with any of the embodiments described herein. The aerosol-generating device is configured to connect to the cartridge assembly and comprises an electric heater for heating the cartridge when the cartridge assembly is connected to the aerosol-generating device. The aerosol-generating device further comprises a power supply and a controller configured to control a supply of electrical power from the power supply to the electric heater. The aerosol-generating device at least partially defines at least one system air inlet, the at least one system air inlet providing fluid communication between the exterior of the aerosol-generating system and each of the first air inlet, the second air inlet and an upstream end of the airflow channel.

The at least one system air inlet may comprise a common air inlet providing fluid communication between the exterior of the aerosol-generating system and each of the first air inlet, the second air inlet and an upstream end of the airflow channel.

The at least one system air inlet may comprise a ventilation air inlet providing fluid communication between the exterior of the aerosol-generating system and the upstream end of the airflow channel, and a mainstream air inlet providing fluid communication between the exterior of the aerosol-generating system and each of the first air inlet and the second air inlet.

The aerosol-generating device may comprise a device housing, wherein the at least one system air inlet extends through the device housing.

The aerosol-generating device may comprise a device housing, wherein the aerosol-generating system is configured so that a first portion of the device housing is spaced apart from a second portion of the cartridge assembly to form a second gap between the first portion of the device housing and the second portion of the cartridge assembly when the cartridge assembly is connected to the aerosol-generating device, wherein the second gap forms the at least one system air inlet. For example, an upstream edge of the cartridge assembly may be spaced apart from an edge of the device housing to form the second gap.

Preferably, the aerosol-generating system is configured so that, during use, the electric heater heats the first compartment and the second compartment to between about 60 degrees Celsius and about 100 degrees Celsius, more preferably between about 70 degrees Celsius and about 90 degrees Celsius, most preferably about 80 degrees Celsius.

Preferably, the aerosol-generating system is configured so that, during use, ventilation air from the airflow channel enters the mixing chamber through the ventilation air inlet at a temperature of less than about 50 degrees Celsius.

The electric heater may comprise a resistive heater. In embodiments in which the cartridge comprises a third compartment positioned between the first compartment and the second compartment, preferably the third compartment is configured to receive the resistive heater when the cartridge assembly is connected to the aerosol-generating device. During use, the controller controls the supply of electrical power from the power supply to the resistive heater to heat the first compartment and the second compartment.

The electric heater may comprise an inductive heater. In embodiments in which the cartridge comprises a third compartment positioned between the first compartment and the second compartment, preferably the cartridge comprises a susceptor material positioned within the third compartment. During use, the controller controls the supply of electrical power from the power supply to the inductive heater to inductively heat the susceptor material, which then heats the first compartment and the second compartment.

The aerosol-generating device may comprise a device cavity configured to receive at least a portion of the cartridge. The inductive heater may comprise at least one induction coil extending around at least a portion of the device cavity. The induction coil may extend completely around the device cavity. The induction coil may be wound around the device cavity with a plurality of windings.

The inductive heater may comprise at least one planar induction coil. Preferably, each planar induction coil comprises a flat spiral induction coil.

As used herein a "flat spiral induction coil" means a coil that is generally planar, wherein the axis of winding of the coil is normal to the surface in which the coil lies. In some embodiments, the flat spiral coil may be planar in the sense that it lies in a flat Euclidean plane. However, the term "flat spiral induction coil" as used herein covers coils that are shaped to conform to a curved plane or other three dimensional surface. For example, a flat spiral coil may be shaped to conform to a cylindrical housing or cavity of the device. The flat spiral coil can then be said to be planar but conforming to a cylindrical plane, with the axis of winding of the coil normal to the cylindrical plane at the centre of the coil. If the flat spiral coil conforms to a cylindrical plane or non-Euclidian plane, preferably, the flat spiral coil lies in a plane having a radius of curvature in the region of the flat spiral coil greater than a diameter of the flat spiral coil.

The power supply may be a battery, such as a rechargeable lithium ion battery. Alternatively, the power supply may be another form of charge storage device such as a capacitor. The power supply may require recharging. The power supply may have a capacity that allows for the storage of enough energy for one or more uses of the device. For example, the power supply may have sufficient capacity to allow for the continuous generation of aerosol for a period of around six minutes, corresponding to the typical time taken to smoke a conventional cigarette, or for a period that is a multiple of six minutes. In another example, the power supply may have sufficient capacity to allow for a predetermined number of puffs or discrete activations.

The invention will be further described, by way of example only, with reference to the accompanying drawings in which.

Figure 1:
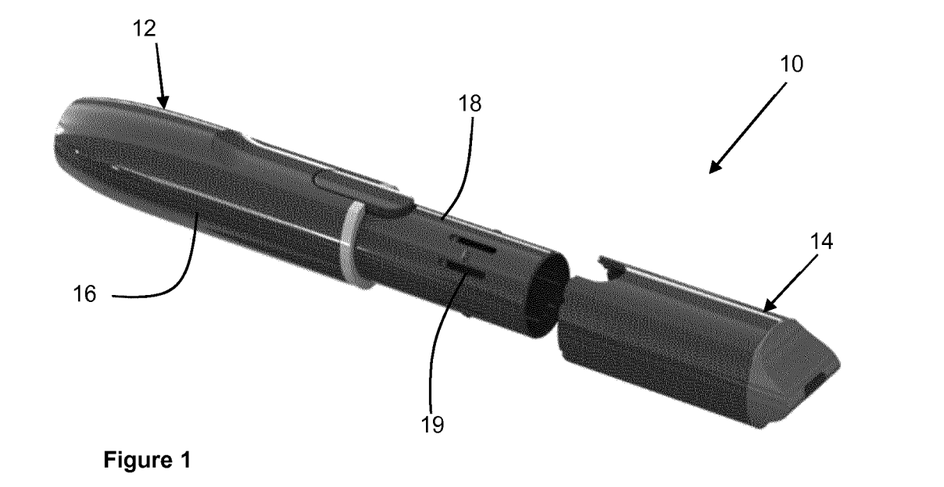
FIG. 1 shows a perspective view of an aerosol-generating system according to an embodiment of the present invention.
Figure 2:
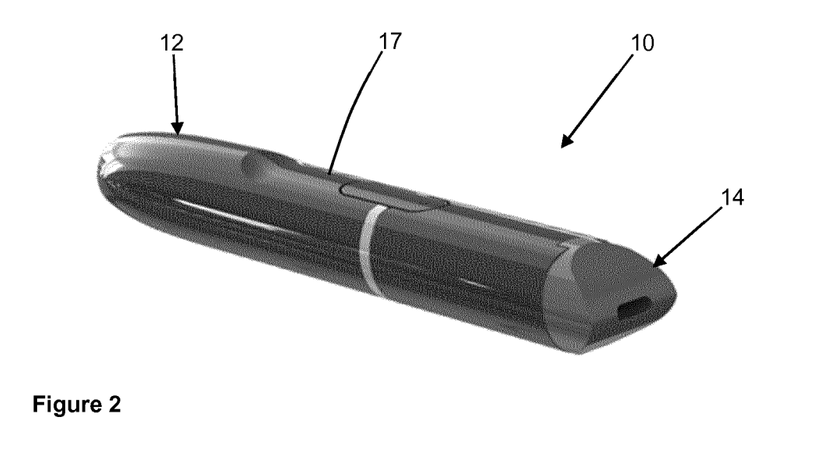
FIG. 2 shows the aerosol-generating system of FIG. 1 with the cartridge assembly coupled to the aerosol-generating device.
Figure 3:
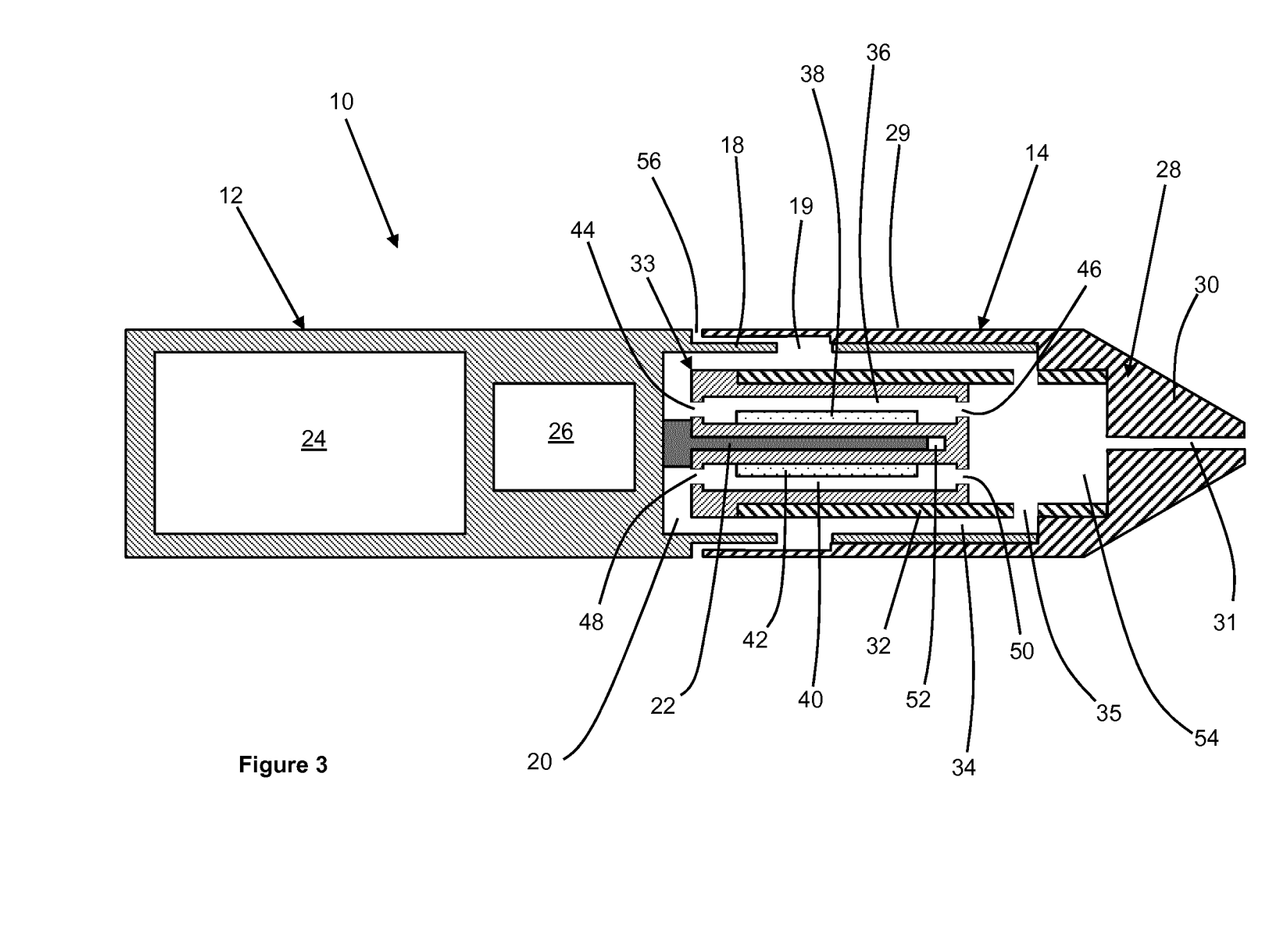
FIG. 3 shows a schematic cross-sectional view of the aerosol-generating system of FIG. 2.

FIG. 1 shows an aerosol-generating system 10 according to an embodiment of the present invention. The aerosol-generating system 10 comprises an aerosol-generating device 12 and a cartridge assembly 14. FIGS. 2 and 3 show the cartridge assembly 14 coupled to the aerosol-generating device 12.

The aerosol-generating device 12 comprises a device outer housing 16, and a device inner housing 18 that defines a device cavity 20 for receiving a portion of the cartridge assembly 14. A plurality of device air inlets 19 extend through the device inner housing 18.

As shown in FIG. 3, which shows a schematic cross-sectional view of the aerosol-generating system 10, the aerosol-generating device 12 further comprises an electric heater 22, a power supply 24, and a controller 26 for controlling a supply of electrical power from the power supply 24 to the electric heater 22. The electric heater 22 is a resistive heater extending into the device cavity 20 at an upstream end of the device cavity 20. The power supply 24 is a rechargeable battery.

The cartridge assembly 14 comprises a mouthpiece 28 comprising a tubular part 29, a downstream part 30, and a mouthpiece air outlet 31. The tubular part 29 is configured to receive the device inner housing 18 in an interference fit to connect the cartridge assembly 14 to the aerosol-generating device 12. The mouthpiece 28 and the device outer housing 16 together form a system outer housing 17.

The cartridge assembly 14 further comprises a cartridge holder 32 and a cartridge 33. The cartridge holder 32 has a tubular shape and comprises a downstream portion that is received within a downstream end of the mouthpiece 28 by an interference fit to secure the cartridge holder 32 to the mouthpiece 28. The remainder of the cartridge holder 32 is spaced apart from the mouthpiece 28 to form an airflow channel 34 therebetween. The airflow channel 34 is sized to receive the device inner housing 18 without blocking the airflow channel 34. A plurality of ventilation air apertures 35 extend through the cartridge holder 32 at a downstream end of the airflow channel 34.

The cartridge 33 defines a first compartment 36 containing a first aerosol-forming substrate 38 and a second compartment 40 containing a second aerosol-forming substrate 42. The first aerosol-forming substrate 38 comprises a nicotine source and the second aerosol-forming substrate 42 comprises an acid source. The first compartment 36 comprises a first air inlet 44 and a first air outlet 46. The second compartment 40 comprises a second air inlet 48 and a second air outlet 50.

The cartridge 33 also defines a third compartment 52 positioned between the first and second compartments 36, 40. A downstream end of the cartridge 33 is spaced apart from the downstream part 30 of the mouthpiece 28 to define a mixing chamber 54.

When the cartridge assembly 14 is connected to the aerosol-generating device 12, a plurality of system air inlets 56 are formed between the cartridge assembly 14 and the aerosol-generating device 12. The cartridge holder 32 and the cartridge 33 are received within the device cavity 20, and the electric heater 22 is received within the third compartment 52.

During use of the aerosol-generating system 10, the controller 26 controls a supply of electrical power from the power supply 24 to the electric heater 22 to energize the electric heater 22. The electric heater 22 heats the first and second aerosol-forming substrates 38, 42.

When a user draws on the downstream part 30 of the mouthpiece 28 air is drawn into the aerosol-generating system 10 through system airflow inlets 56. Air entering the aerosol-generating system 10 through the system airflow inlets 56 enters the device cavity 20 via device airflow inlets 19 extending through the device inner housing 18. Each device airflow inlet 19 is a combined air inlet so that air entering through each device airflow inlet 19 is divided into ventilation air and mainstream air.

The mainstream air is directed to the upstream end of the device cavity 20 where it enters the first and second compartments 36, 40 through the first and second air inlets 44, 48. As the mainstream air flows through the first and second compartments 36, 40, nicotine vapour and acid vapour from the first and second aerosol-forming substrates 38, 42 are entrained in the mainstream air. The mainstream air containing the nicotine vapour and the acid vapour flows into a mixing chamber 54 at a downstream end of the cartridge 33 where the nicotine vapour and the acid vapour react to form nicotine salt particles.

The ventilation air is directed along the airflow channel 34 where it enters the mixing chamber 54 via the ventilation air apertures 35 extending through the cartridge holder 32. The cartridge holder 32 insulates the ventilation air within the airflow channel 34 from the heated cartridge 33 so that the ventilation air entering the mixing chamber 54 is at a significantly lower temperature than the nicotine vapour and acid vapour entering the mixing chamber 54 from the cartridge 33.

In the mixing chamber 54, the ventilation air mixes with the nicotine salt particles formed from the nicotine vapour and the acid vapour to form an aerosol for delivery to the user. The aerosol flows out of the mixing chamber 54 via the mouthpiece air outlet 31, which forms a system airflow outlet.

The invention claimed is:

1. A cartridge assembly for an aerosol-generating system, the cartridge assembly comprising:
    a cartridge having an upstream end and a downstream end, the cartridge comprising:
        a first compartment having a first air inlet at the upstream end of the cartridge and a first air outlet at the downstream end of the cartridge, and
        a second compartment having a second air inlet at the upstream end of the cartridge and a second air outlet at the downstream end of the cartridge;
    a cartridge holder, wherein at least a portion of the cartridge is received within the cartridge holder;
    a mouthpiece having an upstream end and a downstream end, wherein at least a portion of the cartridge holder is received within the mouthpiece, wherein the downstream end of the cartridge is spaced apart from the downstream end of the mouthpiece and defines a mixing chamber between the downstream end of the cartridge and the downstream end of the mouthpiece, and wherein another portion of the cartridge holder is spaced apart from the mouthpiece and defines an airflow channel between the cartridge holder and the mouthpiece; and
    a ventilation air aperture providing fluid communication between a downstream portion of the airflow channel and the mixing chamber.

2. The cartridge assembly according to claim 1, wherein the ventilation air aperture is disposed downstream of the downstream end of the cartridge.

3. The cartridge assembly according to claim 2, wherein the ventilation air aperture is disposed at a downstream end of the airflow channel.

4. The cartridge assembly according to claim 1,
    wherein the cartridge defines a longitudinal direction extending between the upstream end of the cartridge and the downstream end of the cartridge, and a radial direction orthogonal to the longitudinal direction, and
    wherein at least a portion of the airflow channel is disposed radially outward from the cartridge.

5. The cartridge assembly according to claim 1, wherein the mouthpiece comprises:
    a tubular part in which the at least a portion of the cartridge holder is received;
    a downstream part extending across a downstream end of the tubular part; and
    a mouthpiece air outlet in the downstream part, the mouthpiece air outlet providing fluid communication between the mixing chamber and an exterior of the cartridge assembly.

6. The cartridge assembly according to claim 5, wherein at least a portion of a downstream end of the cartridge holder is spaced apart from the downstream part of the mouthpiece and forms a first gap between the downstream end of the cartridge holder and the downstream part of the mouthpiece, the first gap forming the ventilation air aperture.

7. The cartridge assembly according to claim 1, wherein the cartridge holder defines the ventilation air aperture, the ventilation air aperture extending through a part of the cartridge holder.

8. The cartridge assembly according to claim 1, wherein the cartridge holder comprises a tubular part in which the at least a portion of the cartridge is received.

9. The cartridge assembly according to claim 8, wherein the ventilation air aperture extends through a downstream portion of the tubular part of the cartridge holder.

10. The cartridge assembly according to claim 1, wherein the first compartment contains a nicotine source and the second compartment contains an acid source.

11. An aerosol-generating system, comprising:
    a cartridge assembly according to claim 1; and
    an aerosol-generating device configured to connect to the cartridge assembly, the aerosol-generating device comprising:
        an electric heater configured to heat the cartridge when the cartridge assembly is connected to the aerosol-generating device,
        a power supply, and a controller configured to control a supply of electrical power from the power supply to the electric heater, wherein the aerosol-generating device at least partially defines at least one system air inlet, the at least one system air inlet providing fluid communication between an exterior of the aerosol-generating system and each of the first air inlet, the second air inlet, and an upstream end of the airflow channel.

12. The aerosol-generating system according to claim 11, wherein the at least one system air inlet comprises a common air inlet providing fluid communication between the exterior of the aerosol-generating system and each of the first air inlet, the second air inlet, and the upstream end of the airflow channel.

13. The aerosol-generating system according to claim 11, wherein the at least one system air inlet comprises:

a ventilation air inlet providing fluid communication between the exterior of the aerosol-generating system and the upstream end of the airflow channel; and a mainstream air inlet providing fluid communication between the exterior of the aerosol-generating system and each of the first air inlet and the second air inlet.

14. The aerosol-generating system according to claim 11, wherein the aerosol-generating device further comprises a device housing, and wherein the at least one system air inlet extends through the device housing.

15. The aerosol-generating system according to claim 11, wherein the aerosol-generating device further comprises a device housing, wherein the aerosol-generating system is configured so that a first portion of the device housing is spaced apart from a second portion of the cartridge assembly and forms a second gap between the first portion of the device housing and the second portion of the cartridge assembly when the cartridge assembly is connected to the aerosol-generating device, and wherein the second gap forms the at least one system air inlet.

\* \* \* \* \*